(12) United States Patent
Lefebvre et al.

(10) Patent No.: US 8,741,051 B2
(45) Date of Patent: Jun. 3, 2014

(54) COATING COMPOSITION COMPRISING POLYDEXTROSE, PROCESS FOR PREPARING SAME AND USE OF COATING INGESTIBLE SOLID FORMS

(75) Inventors: Sandra Lefebvre, Castres (FR); Gérard Trouve, Castres (FR); Michel Malandain, Fourqueux (FR)

(73) Assignee: Société d'Exploitation de Produits pour les Industries Chimiques SEPPIC, Paris (FR)

( * ) Notice: Subject to any disclaimer, the term of this patent is extended or adjusted under 35 U.S.C. 154(b) by 843 days.

(21) Appl. No.: 12/681,640

(22) PCT Filed: Oct. 1, 2008

(86) PCT No.: PCT/FR2008/051773
§ 371 (c)(1),
(2), (4) Date: Apr. 5, 2010

(87) PCT Pub. No.: WO2009/053576
PCT Pub. Date: Apr. 30, 2009

(65) Prior Publication Data
US 2010/0291311 A1 Nov. 18, 2010

(30) Foreign Application Priority Data
Oct. 5, 2007 (FR) .................................. 07 58091

(51) Int. Cl.
| | | |
|---|---|---|
| *A61K 9/36* | (2006.01) | |
| *A61K 8/73* | (2006.01) | |
| *C08L 1/00* | (2006.01) | |
| *C08L 3/00* | (2006.01) | |
| *C08L 5/00* | (2006.01) | |
| *C09D 101/00* | (2006.01) | |
| *C09D 103/00* | (2006.01) | |
| *C09D 105/00* | (2006.01) | |
| *C09J 101/00* | (2006.01) | |
| *C09J 103/00* | (2006.01) | |
| *C09J 105/00* | (2006.01) | |

(52) U.S. Cl.
USPC ........................ 106/162.1; 424/479; 524/27

(58) Field of Classification Search
USPC ........................ 524/27; 106/162.1; 424/479
See application file for complete search history.

(56) References Cited

U.S. PATENT DOCUMENTS

| | | | |
|---|---|---|---|
| 3,766,165 A | 10/1973 | Rennhard et al. | |
| 3,876,794 A | 4/1975 | Rennhard | |
| 4,513,019 A | 4/1985 | Brancq et al. | |
| 4,665,648 A | 5/1987 | Branco et al. | |
| 4,802,924 A * | 2/1989 | Woznicki et al. | 427/2.15 |
| 5,393,333 A | 2/1995 | Trouve | |
| 5,965,162 A * | 10/1999 | Fuisz et al. | 424/464 |
| 6,210,714 B1* | 4/2001 | Oshlack et al. | 424/476 |
| 6,274,162 B1* | 8/2001 | Steffenino et al. | 424/439 |
| 6,468,561 B1* | 10/2002 | Grillo et al. | 424/480 |
| 6,579,953 B1 | 6/2003 | Gotsche et al. | |
| 6,723,342 B1* | 4/2004 | Augello et al. | 424/479 |
| 7,049,360 B2 | 5/2006 | Angel et al. | |
| 2002/0042466 A1 | 4/2002 | Angel et al. | |
| 2003/0104063 A1* | 6/2003 | Babcock et al. | 424/486 |
| 2003/0215585 A1* | 11/2003 | Bunick | 428/34.1 |
| 2004/0091535 A1* | 5/2004 | Vachon et al. | 424/471 |
| 2004/0241236 A1* | 12/2004 | Li et al. | 424/471 |
| 2005/0107498 A1* | 5/2005 | Kolter et al. | 524/35 |
| 2005/0118217 A1* | 6/2005 | Barnhart et al. | 424/401 |
| 2005/0175696 A1* | 8/2005 | Edgren et al. | 424/470 |
| 2006/0024353 A1 | 2/2006 | Trouve et al. | |
| 2006/0087051 A1* | 4/2006 | Bunick et al. | 264/109 |
| 2007/0098931 A1* | 5/2007 | Bunick | 428/34.1 |
| 2007/0122455 A1* | 5/2007 | Myers et al. | 424/439 |
| 2007/0243257 A1* | 10/2007 | Bedos et al. | 424/486 |
| 2008/0069880 A1* | 3/2008 | Bunick | 424/472 |
| 2008/0075825 A1* | 3/2008 | Fuisz et al. | 426/534 |
| 2008/0166449 A1* | 7/2008 | Kabse et al. | 426/5 |
| 2008/0233174 A1* | 9/2008 | Myers et al. | 424/435 |
| 2008/0248102 A1* | 10/2008 | Rajewski et al. | 424/452 |
| 2009/0074866 A1* | 3/2009 | Chen | 424/481 |
| 2009/0074944 A1* | 3/2009 | Xie et al. | 427/2.14 |

FOREIGN PATENT DOCUMENTS

| | | |
|---|---|---|
| DE | 1 077 430 | 3/1960 |
| DE | 1 081 229 | 5/1960 |
| DE | 1 094 457 | 12/1960 |
| DE | 100 49 297 | 4/2002 |
| EP | 0 133 827 | 3/1985 |
| EP | 1 124 541 | 11/2003 |
| EP | 1 552 819 | 7/2005 |
| EP | 2 197 967 | 11/2011 |
| FR | 2 660 317 | 10/1991 |
| GB | 922 458 | 4/1963 |
| WO | WO 2004 073582 | 9/2004 |

OTHER PUBLICATIONS

International Search Report for PCT/FR2008/051773 of Jun. 9, 2009.
Written Opinion for corresponding PCT/FR2008/051773, Apr. 5, 2010.
Kirk-Othmer's Encyclopedia of Chemical Technology: Sulfonation and sulfation to thorium and thorium compounds, $3^{rd}$ ed., Wiley: Univ. of Michigan 1983, vol. 17, p. 281.

* cited by examiner

*Primary Examiner* — Liam Heincer
(74) *Attorney, Agent, or Firm* — Allen E. White

(57) ABSTRACT

Composition (C) for coating ingestible solid forms, comprising, per 100% of its mass—from 10% to 90% of a graft copolymer of polyvinyl alcohol and of polyethers (Pi), and—from 10% to 90% by mass of an auxiliary coating agent, characterized in that a non-zero mass proportion of said auxiliary agent is polydextrose. Processes for the preparation and use thereof.

14 Claims, No Drawings

COATING COMPOSITION COMPRISING POLYDEXTROSE, PROCESS FOR PREPARING SAME AND USE OF COATING INGESTIBLE SOLID FORMS

FIELD OF THE INVENTION

This application is a 371 of International PCT Application PCT/FR2008/051773, filed Oct. 1, 2008, the entire contents of which are incorporated herein by reference.

The subject of the present invention is film-forming compositions for the colored and glossy coating of ingestible solid forms, and more particularly pharmaceutical tablets for gastric use, the processes for preparing said film-forming compositions, the coating processes using said film-forming compositions and the colored and glossy coated pharmaceutical products obtained by implementing the coating processes comprising the use of said film-forming compositions.

RELATED ART

The film-coating of tablets with colored polymer films is commonly used in the pharmaceutical industry. Improving the external appearance of these tablets, in order to obtain a glossy external appearance, constitutes an economic challenge. The reason for this is that, in addition to a purely esthetic consideration which allows a glossy tablet to be considered as being a tablet of advanced quality, it is also established that the glossiness of tablets reduces the apprehension of patients who have difficulties in swallowing and ingesting tablets, and consequently enables reinforced medical adherence to prescriptions. The term "glossiness" is intended to mean the result of one of the interactions of light with matter. When light hits an object, the majority of the light penetrates the object and a small portion of the light is reflected at the surface of the object. This surface-reflected light is the visible attribute known as "glossiness". For a glossy surface, the angle of the beam of reflected light (known as the "mirror angle") is equal to the angle of the incident light. For a matt surface, the light is reflected at numerous angles instead of just the mirror angle as in the case of a glossy surface.

Coating processes and film-forming products that allow glossy films to be obtained exist in the prior art. Sugar-coating processes enable tablets with a glossy appearance to be obtained, but these are relatively uneconomical processes, which consist of a succession of several consecutive steps. Dragées are galenical forms constituted of a central core surrounded by a thick sugar-based protective coat. The core may be an almond, a dried fruit or a chocolate chip for dragées used in confectionary, or else a mini-tablet containing one or more medicinal active principle(s) for dragées used in pharmacy. The protective layer is generally constituted of sugar (sucrose) and of a filler such as talc. It is formed by successive applications of clear sugar syrup and of fillers in rotary drums, each application of syrup and of filler being followed by a drying step. The sugar syrups are obtained by dissolving sucrose in hot water with stirring; they contain a high concentration of sugar, up to approximately 70% to 80% by weight, in order to minimize the amounts of water to be evaporated off. Dragées are colored by means of a sugar syrup colored with pigments, lakes or dyes that are permitted in the field of application. This colored syrup is applied at the end of assembly of the dragée, thereby avoiding bulk coloration. Finally, to obtain a dragée with a glossy appearance, a polishing or brightening step is carried out using a dispersion of wax such as carnauba wax or beeswax. These processes for the assembly and polishing of dragées have been known for a long time, are described, for example, in Kirk-Othmer's encyclopedia (3rd edition, volume 17, page 281), and their duration makes them relatively uneconomical processes. Film-coating processes are faster than sugar-coating processes since the amounts of film deposited are smaller; they represent only 3% to 5% of the mass of substrate coated. However, they necessitate the use of particular equipment consisting of a spraying device associated with an efficient drying system, since the amounts of water to be evaporated off are considerable. The film-coating processes comprise the preparation of a dispersion, preferably an aqueous dispersion, containing a film-forming polymer, a coloring system, preferably pigments or lakes, and optionally a plasticizer, fillers and/or technological additives, followed by the spraying of said dispersion on to the tablets that are in motion in a perforated rotary drum or in a fluidized bed. A stream of hot air, entering at a temperature greater than or equal to 40° C., dries the sprayed dispersion and causes coalescence of the film around the tablets. The deposited film has a thickness of a few tens of microns; it is opaque and uniformly colored. The film-forming polymers most commonly used are acrylic or cellulose derivatives. Acrylic film-forming polymers are mainly used for preparing film-coated forms intended for enteric use or for use involving sustained release of the medicinal active ingredient. However, they prove to be relatively unstable for preparing glossy film-coated forms intended to be dissolved in a gastric medium. Cellulose-based film-forming polymers are therefore preferred for the preparation of film-coating compositions intended for preparing film-coated forms that need to be dissolved in a gastric medium. The term "cellulose-based film-forming polymer" is intended to denote mainly edible polymers chosen from cellulose derivatives such as, for example, cellulose alkyl ethers, cellulose hydroxyalkyl ethers, cellulose monocarboxylic esters and mixed cellulose ethers. Among these products mention may be made of hydroxypropyl-methylcelluloses (HPMCs), ethylcelluloses (ECs), methylcelluloses (MCs), carboxymethylcelluloses, hydroxypropylcelluloses (HPCs) or cellulose acetates or phthalates, as described, for example, in the European patent application published under the number EP 0 133 827 A1. Use may thus be made of cellulose-based film-forming polymers that are already sold in granulated form, such as, for example, the granulated HPMC known under the name Pharmacoat™ G. Use may also be made of mixtures of different cellulose-based film-forming polymers, such as, for example, HPMC/EC mixtures. U.S. Pat. No. 6,468,561 also teaches the use of polydextrose in film-forming compositions, comprising, for example, cellulose-based film-forming polymers, for improving the adhesion of the coating film to the surface to which the film-forming compositions are applied and for eliminating the unpleasant taste sensation in the mouth of patients, which is experienced with the other sugar derivatives normally used. However, the films obtained while using such cellulose-based polymers do not make it possible to obtain a satisfactory glossy appearance, and it is then necessary to add an additional step of polishing of the film-coated form using a wax, which then results in a significant increase in the cost of the film-coating process. This additional polishing step can be avoided by adding to the film-forming composition particular pigments such as titanium oxides, and more particularly the titanium-micas described, for example in the international patent application published under the number WO 2004/073582, sold by the company Merck under the name Candurin™ Silver fine, Candurihn™ Silver Luster, Candurin™ Red Shimmer or Candurin™ Sparkle Silvers. However, the visual effect obtained on the film-coated forms prepared by using the film-coating compositions comprising these pigments is a metalized pearlescent effect and not a glossy effect. The term "pearlescence" is intended to mean a color that deploys different colors depending on the angle of illumination and on the angle of observation, in the same manner as nacre. The pearlescence is calculated by measuring the color change (DE) at angles of observation of 15° and at a temperature of 25° C. relative to the specular reflection. International publication WO 2004/073582 expressly discloses a pearlescent effect provided through the use of the particular pigments described previously, rather than a gloss effect. Moreover, cellulose-based film-forming polymers rapidly form viscous solutions in water and can only be used in mass proportions of 10% to 15% relative to 100% of the mass of the film-coating composition in order to produce solutions that are sprayable in the film-coating process. The use of such mass proportions of film-forming cellulose-based polymers then necessitates the evaporation of large amounts of water during the film-coating process, which lengthens the duration and increases the cost. Film-forming polymers that lead to a lower viscosity in aqueous solution constitute an alternative to the use of cellulose-based film-forming copolymers for preparing film-coating forms. European patent EP 1 124 541 B1 describes the use of grafted polymers that are water-soluble or that are water-dispersible, as coating agents, binders and/or film-forming adjuvants in pharmaceutical galenical forms. These grafted copolymers can be obtained by copolymerization of at least one vinyl ester of $C_1$-$C_{24}$ aliphatic carboxylic acids in the presence of polyethers. American patent application US 2005/0107498 A1 describes compositions for film-coating solid forms, which can be readily solubilized in water or readily dispersed in water, thus leading to a reduced preparation time for the film-coating aqueous solutions or aqueous dispersions, which can be readily sprayed without blocking the nozzles during the spraying step of the process for preparing the film-coated form. These film-coating compositions are composed of grafted copolymers obtained by copolymerization of polyvinyl alcohol and of polyethers, of auxiliaries containing hydroxyl, amide or ester functions and of film-coating adjuvants. The film-coating composition described in application US 2005/0107498 A1 does not completely solve the stated problem, since it leads to the production of film-coated forms with a matt rather than a glossy appearance.

This is why the inventors have sought to develop novel film-forming compositions which dissolve rapidly in water or disperse rapidly in water, to allow the preparation of film-coated solid forms intended for gastric use, which have a glossy appearance according to a quick and economical process.

SUMMARY OF THE INVENTION

The present invention provides a coating composition (C) that includes, per 100% of its mass from 10% to 90% by mass of a grafted copolymer of polyvinyl alcohol and of polyethers ($P_1$), and from 90% to 10% by mass of an auxiliary coating agent in which a non-zero mass proportion of the auxiliary agent is polydextrose, and in that the ratio by mass of the grafted copolymer ($P_1$) to the polydextrose is less than or equal to 3. The present invention further provides a process for producing the same and a process for preparing coated solid forms.

DETAILED DESCRIPTION OF THE INVENTION

According to a first aspect, a subject of the invention is a coating composition (C) comprising, per 100% of its mass:
from 10% to 90% by mass of a grafted copolymer of polyvinyl alcohol and of polyethers ($P_1$), and
from 90% to 10% by mass of an auxiliary coating agent, characterized in that a non-zero mass proportion of said auxiliary agent is polydextrose, and in that the ratio by mass of the grafted copolymer ($P_1$) to the polydextrose ($P_2$) is less than or equal to 3.

The term "grafted copolymer of polyvinyl alcohol and of polyethers WO" denotes the copolymers obtained by copolymerization:
of at least one vinyl ester of aliphatic carboxylic acids containing from one to 24 carbon atoms, preferably vinyl acetate,
with at least one polyether of formula (I):

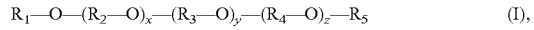
$$R_1-O-(R_2-O)_x-(R_3-O)_y-(R_4-O)_z-R_5 \qquad (I),$$

in which $R_1$ represents a hydrogen atom or else a linear or branched alkyl radical containing from 1 to 24 carbon atoms, or else an acyl radical of formula $R_6-C(=O)-$, in which $R_6$ is a hydrocarbon-based radical containing from 1 to 23 carbon atoms, or else a polyvinyl alcohol residue. According to one particular aspect, $R_1$ is a hydrogen atom or a methyl radical; $R_5$ represents a hydrogen atom, or else a linear or branched alkyl radical containing from 1 to 24 carbon atoms, or else an acyl radical of formula $R_6-C(=O)-$, in which $R_6$ is a hydrocarbon-based radical containing from 1 to 23 carbon atoms, $R_5$ more particularly representing a hydrogen atom.

$R_2$, $R_3$ and $R_4$, which may be identical or different, represent, independently of one another, a radical chosen from the groups having the formulae:
- $-(CH_2)_n-$ for which n is an integer between 2 and 4;
- $-CH_2-CH(CH_3)-$;
- $-CH_2-CH(CH_2-CH_3)-$;
- $-CH_2-CH-OR_7-CH_2-$ for which $R_7$ represents a hydrogen atom, or else a linear or branched alkyl radical containing from 1 to 24 carbon atoms, or else an acyl radical of formula $R_6-C(=O)-$, in which $R_6$ is a hydrocarbon-based radical containing from 1 to 23 carbon atoms; $R_2$, $R_3$ and $R_4$ being preferentially chosen from $-(CH_2)_2-$ and $-CH_2-CH(CH_3)-$;
- x is a number between 1 and 5000, more particularly between 10 and 2000, and most particularly between 20 and 500;
- y is a number between 0 and 5000,
- z is a number between 0 and 5000,
- y and z being preferentially chosen to be equal to 0 when x is greater than 10.

Calculation of the molecular weight of the polyether of formula (I) from the values of x, y and z makes it possible to obtain a mean value, although such products have a broad molecular weight distribution.

The polyethers of formula (I) preferentially used are those of which the average molecular weight is between 400 and 50 000 g·mol$^{-1}$, and more preferentially those of which the average molecular weight is between 1500 and 20 000 g·mol$^{-1}$.

The polyvinyl ester groups of the grafted copolymers of polyvinyl alcohol and of polyethers are then fully or partially hydrolyzed.

The preparation of such grafted copolymers is described, for example, in the German patent applications published under the numbers DE 1 077 430, DE 1 094 457 and DE 1 081 229. Such grafted copolymers are, for example, sold under the name Kollicoat™.

The term "auxiliary coating agent" denotes compounds or mixtures of compounds that are water-soluble or water-dispersible, chosen from the group comprising polymers containing hydroxyl, amide or ester functions, and organic compounds of low molecular mass. The auxiliary coating agents are in accordance with the regulations in force in the pharmaceutical, dietetic or food sectors.

The polymers containing hydroxyl, amide or ester functions that are used as auxiliary coating agents are in general chosen from:
polyvinyl alcohols, polysaccharides, celluloses, starches, lactic acid polymers, polyethylene glycols, polypropylene glycols or block copolymers comprising polyethylene glycols and polypropylene glycols, and also derivatives thereof;
polyvinylpyrrolidones and copolymers of vinylpyrrolidone and of vinyl acetate;
copolymers of vinylpyrrolidone and of methacrylic acid, and copolymers of vinylpyrrolidone and of acrylic acid;
(meth)acrylic copolymers and hydroxyalkyl(meth)acrylic copolymers such as those described in the German patent application published under the number DE 1 009 9297, and polyvinyl acetates; and
gelatin.

According to one particular aspect of the present invention, the polymers containing hydroxyl, amide or ester functions that are used as auxiliary coating agents are chosen from polyvinyl alcohols with a degree of hydrolysis of between 80 mol % and 99 mol %, hydroxypropylmethylcelluloses (HPMCs), hydroxypropyl-celluloses (HPCs), hydroxyethylmethylcelluloses, methylcelluloses, sodium carboxymethylcelluloses, amylose, maltodextrins, glucose syrups, cyclodextrins, dextrans, inulin, polyfructose, alginates such as propylene glycol alginate, pectins, carraghenates, guar, xanthan gums, gum arabics, terpolymers of butyl methacrylate and of 2-(dimethylamino)ethyl methacrylate and of methyl methacrylate, copolymers of methacrylic acid and of ethyl acrylate, chitosans, ethylcelluloses, crosslinked polyvinylpyrrolidones, polyvinyl acetate, and celluloses, and more particularly microcrystalline celluloses.

The polydextrose used in a non-zero mass proportion of said auxiliary coating agent is a water-soluble polysaccharide obtained by polymerizing glucose, or dextrose, of which the characteristics and the methods of preparation are described in the American patents published under the U.S. Pat. Nos. 3,766,165 and 3,876,794. The polydextrose is commercially available.

The organic compounds of low molecular mass used as auxiliary coating agents are in general chosen from urea, sugars, sugar-based alcohols, sugar derivatives or sugar-based alcohol derivatives and silicas of which the specific surface area is greater than or equal to 100 $m^2g^{-1}$. The organic compounds of low molecular mass used as preferred auxiliary coating agents are lactose, sucrose, glucose, mannitol, sorbitol, isomalt and xylitol.

According to one particular aspect, the coating composition (C) as defined above, also comprises, per 100% of its mass, from 2% to 30% by mass of a plasticizer or of a mixture of plasticizers.

The term "plasticizer" is mainly intended to mean either soluble edible plasticizers such as polyols in general and more particularly sorbitol, mannitol, xylitol, glycerol, sucrose, polyethylene glycols or polypropylene glycols, or sparingly water-soluble edible plasticizers such as those comprising an aliphatic chain containing at least 12 carbon atoms, for example stearic acid, stearic acid salts, for instance magnesium stearate or aluminum stearate, polyethoxylated stearic acid, fatty acid mono-glycerides, fatty acid diglycerides and derivatives thereof esterified with acetic acid, tartaric acid or lactic acid, fatty acid esters of propylene glycol, fatty acid esters of sorbitol, fatty acid esters of sorbitan, fatty acid esters of mannitol, fatty acid esters of mannitan or certain sucroesters, sucroglycerides or polyglycerol esters, in particular those characterized by an HLB number of less than 7.

According to another particular aspect, the coating composition (C) as defined above also comprises, per 100% of its mass, from 2% to 30% by mass of one or more coloring agents.

The term "coloring agent" used in the invention mainly denotes dyes or pigments, for instance those mentioned in the European or US pharmacopeias, or in the list of food additives, referenced in Europe under the numbers E100 to E172, for instance iron oxides, titanium oxides, zinc oxides or magnesium oxides, dyes absorbed onto alumina lakes, titanium micas, or certain natural dyes such as caramel, carotenoids, riboflavin, indigotin, carmine or chlorophyll. Composite dyes constituted of an assembly of potassium aluminum silicates (mica), of titanium dioxide and of dyes, such as those sold by Merck under the name Candurin™ may also be advantageously used.

According to another particular aspect, the coating composition (C) as defined above also comprises, per 100% of its mass, from 2% to 30% by mass of one or more inert fillers.

The inert fillers used in the invention are those which make it possible to modify the properties of the coating material and to protect said material. By way of example of inert fillers, mention may be made of opacifiers, for instance talc, kaolin and titanium oxide; food-grade wetting and dispersing surfactants, for instance sorbitan esters, ethoxylated sorbitan esters, ethoxylated hydrogenated castor oils, sodium lauryl sulfate, ethoxylated fatty alcohols and ethoxylated fatty acids; antifoams and foam-reducing agents such as fatty acids, silicones and silicone derivatives; diluents, for instance lactose, sucrose, mannitol, xylitol, isomalt or talc; calcium hydrogen phosphate; magnesium stearate; glyceryl monostearate.

According to another particular aspect, the composition (C) as defined above also comprises from 1% by mass to 20% by mass of a glidant, for example a finely divided colloidal silica such as those sold by the company Degussa under the name Aerosil™. The auxiliary coating agents as defined above themselves occasionally have the property of promoting the flow of the coating compositions in the form of powders or granules, and in this case, it is not necessary to add another glidant.

According to another particular aspect of the present invention, the ratio by mass of the grafted copolymer (P1) to the polydextrose used in the coating composition (C) is greater than or equal to 1/3, and more particularly greater than or equal to 2/3.

According to another particular aspect of the present invention, the ratio by mass of the grafted copolymer (P1) to the polydextrose used in the coating composition (C) is less than or equal to 3, and more particularly less than or equal to 3/2.

Examples of coating compositions (C) include compositions for which the ratio by mass of the grafted copolymer (P1) to the polydextrose is between 2/3 and 3/2.

The comparative tests below show that, when this ratio by mass is greater than 3 (it is 4.5 for product 2, and 7 for product 3, see table A), the gloss is much lower than that obtained for a composition for which this ratio is between 1/3 and 3 (it is 1.17 for product 1), as is summarized in table B.

TABLE A

Comparative tests

| | Product 1 | Product 2 | Product 3 |
|---|---|---|---|
| PVA-PEG copolymer ($P_1$) | 35% | 45% | 70% |
| Polydextrose ($P_2$) | 30% | 10% | 10% |
| Kaolin | 20% | 30% | |

TABLE A-continued

Comparative tests

|  | Product 1 | Product 2 | Product 3 |
|---|---|---|---|
| Pigments (red iron oxide + TiO$_2$) | 15% | 15% | 20% |
| % solids in the film-coating solution | 25% | 25% | 25% |
| P$_1$/P$_2$ ratio by mass | 1.17 | 4.5 | 7 |

Preparation of Dispersions

The film-coating products are dispersed at 25% in water. For each product, 600 g of dispersion are prepared: 150 g of product are dispersed in d50 g of purified water at ambient temperature. The dispersing is carried out using a Turbotest V2004 laboratory stirrer (Rayneri) and a deflocculating turbomixer. The stirring speed is adjusted so as to prevent incorporation of air into the dispersion, thereby making it possible to avoid the formation of foam. After stirring for 45 minutes, the dispersions are ready.

Film-Coating

The dispersions are sprayed onto placebo tablets in a Driacoater 500 perforated film-coating drum (load=3 kg of cores). The following operating conditions are used: air flow rate=300 m$^3$/h; dry air input temperature=55° C.-60° C. The temperature of the cores varies between 36° C. and 38° C. during the film-coating. A theoretical dry deposit of 3% is applied to the tablets.

TABLE B

|  | Product 1 | Product 2 | Product 3 |
|---|---|---|---|
| Gloss density | 990 | 80 | 130 |

According to another particular aspect, a subject of the invention is a coating composition (C) as defined above, characterized in that it is in a ready-to-use form containing the mixtures of its various constituents in the form of an aqueous dispersion, a powder or ready-to-use granules.

The term "aqueous dispersion" is intended to mean dispersions prepared in water or mixtures of water and of water-soluble alcohols, for instance ethanol.

Ready-to-use compositions have several advantages:
handling, storage and checking of a single product;
better reproducibility of the colors and performance qualities;
easier dispersion.

A subject of the invention is also a process for preparing a coating composition (C) as defined above, which is in the form of a dry powder, comprising the following steps:

a step (a) of mixing the grafted copolymer (P$_1$), the polydextrose and, if necessary or if desired, one or more other auxiliary coating agents, one or more plasticizers, one or more coloring agents, one or more inert fillers and/or one or more glidants, a step (b) of grinding the mixture obtained from step (a) so as to form said composition (C).

In the process as defined above, for the implementation of step (a), all the components are added sequentially or simultaneously. The mixing is then generally carried out with a device of bar mixer type.

Step (b) of the process as defined above is, for example, carried out by means of a knife mill so as to obtain a finely divided powder, or with a cryomilling device generally in liquid nitrogen. Such a device makes it possible to optimize the final particle size of the coating composition (C).

A subject of the invention is also a process for preparing a coating composition (C) as defined above, which is in the form of ready-to-use granules, comprising the following steps:

a step (a1) of wetting the grafted polymer (P$_1$) and the polydextrose, optionally with, if necessary or if desired, one or more other auxiliary coating agents, one or more plasticizers, one or more coloring agents, one or more neutral fillers and/or one or more glidants, using a binder solution, in order to obtain a wet mass containing from 30% to 60% water, a step (b1) of drying the wet mass obtained in step (a1), and if desired, or if necessary, a step (c1) of calibrating the dried mass obtained in step (b1) so as to obtain said composition (C).

The process as defined above is, for example, described in the French patent applications published under the numbers FR 2 548 675 and FR 2 660 317, or in Kirk Othmer's encyclopedia (3rd edition, volume 17, page 281).

The term "granules" is mainly intended to mean aggregates of several tens or so, to several thousand particles of matter, which are initially individualized, which may be identical or different in nature.

Steps (a1) and (b1) of the process as defined above are in particular carried out in a mixer-granulator or in a fluidized bed.

Step (c1) of the process as defined above is in particular carried out in an oven or in a fluidized bed.

A subject of the invention is also a process for preparing a coating composition (C) as defined above, which is in the form of ready-to-use granules, comprising the following steps:

a step (a2) of homogenizing the grafted copolymer (P$_1$) and the polydextrose, with, if necessary or if desired, one or more other auxiliary coating agents, one or more plasticizers, one or more coloring agents, one or more inert fillers and/or one or more glidants, in an air-blown fluidized bed, a step (b2) of gradual spraying with water of the fluidized mixture resulting from step (a2) until a wet mass is formed, and a step (c2) of drying the wet mass resulting from step (b2) by blowing with hot air, so as to obtain said composition (C).

In the process as defined above, the hot air is generally at a temperature of between 70° C. and 100° C.

Such a process is, for example, described in the patent application published under the number EP 1 552 819.

A subject of the invention is also the use of the coating composition (C), as defined above, for coating ingestible solid forms.

The term "ingestible solid form" denotes solid forms that can be ingested by humans or animals, irrespective of their intended use, whether they are medicaments, food supplements or forms for cosmetic, confectionery or sweetmeat purposes. The use of the coating composition (C), as defined above, is more particularly intended for tablets.

A subject of the invention is also a process for coating ingestible solid forms, comprising:

a step (a3) of dispersing:
either the grafted copolymer the polydextrose and, if necessary or if desired, one or more other auxiliary coating agents, one or more plasticizers, one or more coloring agents, one or more inert fillers and/or one or more glidants, in a suitable solvent such as an aqueous medium, or the composition (C) as defined above, so as to form a dispersion ($D_1$);

a step (b3) of spraying the dispersion ($D_1$) obtained in step (a3) in which the solutions or the dispersions thus obtained in step (a3) are sprayed onto solid substrates to be coated.

In step (a3) of the process as defined above, the various constituents are maintained in dispersion using a stirrer and a deflocculating turbomixer, while at the same time avoiding the formation of foam.

In step (a3) of the process as defined above, the coating composition (C) represents between 6% and 30% of 100% of the mass of said dispersion ($D_1$).

Finally, a subject of the invention is the dispersion ($D_1$) obtained in step (a3) of the process as defined above.

The use of the coating composition (C) according to the processes described above, makes it possible to prepare coated pharmaceutical products for gastric use, which have a glossy appearance. The following examples illustrate the invention without, however, limiting it.

A—Preparation of Coating Compositions According to the Invention

Composition ($C_1$)

A coating composition ($C_1$) is prepared by successively adding, at ambient temperature 48 g of a grafted copolymer ($P_1$) of polyvinyl alcohol and of polyethylene glycol (PVA/PEG), sold under the name Kollicoat™ IR by the company BASF, 30 g of polydextrose, 24 g of kaolin and 18 g of a mixture of red iron oxide and of titanium oxide, to 480 g of purified water at a temperature of 25° C. Dispersion is carried out using a Turbotest™ V2004 laboratory stirrer (Rayneri) and a deflocculating turbomixer. The stirring speed is adjusted so as to avoid incorporating air into the dispersion, so as not to form any foam. After stirring for 45 minutes, 600 g of composition ($C_1$) are obtained in the form of an aqueous dispersion, in which the mass proportion of solids represent 20%.

Composition ($C_2$)

A coating composition ($C_2$) is prepared by successively adding, at ambient temperature, 36 g of Kollicoat™ IR, 30 g of polydextrose, 12 g of hydroxypropyl-methylcellulose (HPMC) 6 mPas, 24 g of kaolin and 18 g of a mixture of red iron oxide and of titanium oxide, to 480 g of purified water. Dispersion is carried out using a Turbotest™ V2004 laboratory stirrer and a deflocculating turbomixer. The stirring speed is adjusted so as to avoid incorporating air into the dispersion, so as not to form any foam. After stirring for 45 minutes, composition ($C_2$) is obtained in the form of an aqueous dispersion, in which the mass proportion of solids represents 20%.

Composition ($C_3$)

A coating composition ($C_3$) is prepared by successively adding, at ambient temperature, 36 g of Kollicoat™ IR, 42 g of polydextrose, 19.2 g of kaolin, 4.8 g of a polyethylene glycol with an average molecular weight of 400 (PEG 400) and 18 g of a mixture of red iron oxide and of titanium oxide, to 480 g of purified water. Dispersion is carried out using a Turbotestm V2004 laboratory stirrer and a deflocculating turbomixer. The stirring speed is adjusted so as to avoid incorporating air into the dispersion, so as not to form any foam. After stirring for 45 minutes, composition ($C_3$) is obtained in the form of an aqueous dispersion, in which the mass proportion of solids represents 20%.

Composition ($C_4$)

A coating composition ($C_4$) is prepared by successively adding, at ambient temperature, 45 g of Kollicoat™ IR, 75 g of polydextrose, 7.5 g of kaolin, and 22.5 g of a mixture of red iron oxide and of titanium oxide, to 450 g of purified water. Dispersion is carried out using a Turbotest™ V2004 laboratory stirrer and a deflocculating turbomixer. The stirring speed is adjusted so as to avoid incorporating air into the dispersion, so as not to form any foam. After stirring for 45 minutes, composition (C4) is obtained in the form of an aqueous dispersion, in which the mass proportion of solids represents 25%.

Composition ($C_5$)

A coating composition ($C_5$) is prepared by successively adding, at ambient temperature, 27 g of Kollicoat™ IR, 45 g of polydextrose, 4.5 g of kaolin, and 13.5 g of a mixture of red iron oxide and of titanium oxide, to 510 g of purified water. Dispersion is carried out using a Turbotest™ V2004 laboratory stirrer and a deflocculating turbomixer. The stirring speed is adjusted so as to avoid incorporating air into the dispersion, so as not to form any foam. After stirring for 45 minutes, composition ($C_5$) is obtained in the form of an aqueous dispersion, in which the mass proportion of solids represents 15%.

B—Preparation of Coating Compositions According to the Prior Art

Composition ($T_1$)

A coating composition ($T_1$) is prepared by successively adding, at ambient temperature, 48 g of Kollicoat™ IR, 30 g of microcrystalline cellulose, 24 g of kaolin and 18 g of a mixture of red iron oxide and of titanium oxide, to 480 g of purified water. Dispersion is carried out using a Turbotest™ V2004 laboratory stirrer and a deflocculating turbomixer. The stirring speed is adjusted so as to avoid incorporating air into the dispersion, so as not to form any foam. After stirring for 45 minutes, composition ($T_1$) is obtained in the form of an aqueous dispersion, in which the mass proportion of solids represents 20%.

Composition ($T_2$)

A coating composition ($T_2$) is prepared by successively adding, at ambient temperature, 48 g of HPMC (6 mPas), 42 g of microcrystalline cellulose, 12 g of ethoxylated stearic acid comprising 40 mol of ethylene oxide, and 18 g of a mixture of red iron oxide and of titanium oxide, to 480 g of purified water. Dispersion is carried out using a Turbotest™ V2004 laboratory stirrer and a deflocculating turbomixer. The stirring speed is adjusted so as to avoid incorporating air into the dispersion, so as not to form any foam. After stirring for 45 minutes, composition ($T_2$) is obtained in the form of an aqueous dispersion, in which the mass proportion of solids represents 20%.

Composition ($T_3$)

A coating composition ($T_3$) is prepared by successively adding, at ambient temperature, 66 g of Kollicoat™ TR, 8 g of HPMC (6 mPas), 24 g of kaolin, 2.4 g of microcrystalline cellulose and 18 g of a mixture of red iron oxide and titanium oxide, to 480 g of purified water. Dispersion is carried out using a Turbotest™ V2004 laboratory stirrer and a deflocculating turbomixer. The stirring speed is adjusted so as to avoid incorporating air into the dispersion, so as not to form any foam. After stirring for 45 minutes, composition ($T_3$) is obtained in the form of an aqueous dispersion, in which the mass proportion of solids represents 20%.

Composition ($T_4$)

A coating composition ($T_4$) is prepared by successively adding, at ambient temperature, 23.04 g of sodium carboxymethylcellulose (Na CMC), 9.12 g of maltodextrin, 4.8 g of dextrose, 3.84 g of lecithin and 7.2 g of a mixture of red iron oxide and of titanium oxide, to 552 g of purified water at a temperature of 25° C. Dispersion is carried out using a Turbotestm V2004 laboratory stirrer and a deflocculating turbomixer. The stirring speed is adjusted so as to avoid incorporating air into the dispersion, so as not to form any foam. After stirring for 45 minutes, composition ($T_4$) is obtained in the form of an aqueous dispersion, in which the mass proportion of solids represents 8%.

C—Preparation of Coated Solid Forms

The coating compositions $C_1$, $C_2$, $C_3$, $C_4$ and $C_5$ according to the invention and $T_1$, $T_2$, $T_3$ and $T_4$ of the prior art are sprayed onto 3 kg of placebo tablets placed in a Dricoater™ 500 perforated film-coating drum. The flow rate of drying air circulating in the drum is set at 300 m$^3$·h$^1$, and the drum input temperature of the drying air is set at a temperature of between 55° C. and 60° C. The temperature of the cores ranges, in the film-coating preparation operation, between 36° C. and 38° C. A theoretical dry deposit of 3% by mass per 100% of the mass of the tablet is applied to the tablets.

The coating compositions $C_1$, $C_2$, $C_3$, $C_4$ and $C_5$ according to the invention and $T_1$, $T_2$, $T_3$ and $T_1$ of the prior art, prepared in the preceding examples, are used to prepare, respectively, the coated tablets $E_{C1}$, $E_{C2}$, $E_{C3}$, $E_{C4}$, $E_{C5}$ according to the invention and $E_{T1}$, $E_{T2}$, $E_{T3}$ and $E_{T4}$ according to the prior art.

D—Measurement of the Gloss of the Coated Tablets

1—Using a Glossmeter

Glossmeters are used to measure the gloss of the film-coated tablets. They are based on the principle that consists in projecting a beam of light onto the surface to be analyzed, and in measuring the intensity of the light reflected at an angle symmetrical to the angle of incidence.

Instruments dedicated to measuring gloss on curved surfaces such as the surface of tablets are also available. They are based on the same measuring principle as described previously, but using a high-resolution video imaging system. During the measurement, each tablet is illuminated with a powerful light source of daylight type. The light reflected by the tablet is image-analyzed and broken down into:

specular reflection (which gives the gloss effect)
diffuse reflection (which gives the color).

2—Using a Visual Method

The coated tablets, the gloss of which it is desired to evaluate, are placed side by side in an open container placed under natural daylight. A representative panel of ten users duly trained for this evaluation examines the coated tablets arranged under the same conditions. Each member of the panel independently selects, without communicating his or her selection to the other members of the panel, the coated tablet which appears to him or her to have the strongest gloss appearance. Each member of the panel can make only one possible selection. The selections are then collected so as to determine the coated tablets that receive the largest number of selections by the members of the panel.

3—Results Obtained with a Glossmeter

The gloss of the coated tablets $E_{C1}$, $E_{T1}$, $E_{T2}$, $E_{C2}$, $E_{C3}$/and $E_{T3}$, expressed by the degree of gloss thereof, is evaluated according to the principle described in the preceding paragraph 1, using a high-resolution digital camera. The results obtained are reported in table 1 below:

TABLE 1

| | Coated tablet | | | | | |
|---|---|---|---|---|---|---|
| | $E_{C1}$ | $E_{T1}$ | $E_{T2}$ | $E_{C2}$ | $E_{C3}$ | $E_{T3}$ |
| Degree of gloss | 0.77 | 0.61 | 0.58 | 0.77 | 0.80 | 0.60 |
| Gloss density | 1707 | 705 | 1188 | | | |

These results demonstrate that table $E_{C1}$, coated using composition $C_1$, characterized by a ratio by mass of the grafted copolymer (PVA/PEG) to the polydextrose of 1.6, has a degree of gloss of 0.77, which is 26.2% greater than the degree of gloss of tablet $E_{T1}$ coated using composition $T_1$ free of polydextrose, and 32.8% greater than the degree of gloss of tablet $E_{T2}$ coated using composition $T_3$ free of both polydextrose and of grafted copolymer (PVA/PEG).

Similarly, tablets $E_{C2}$ and $E_{C3}$, coated using compositions $C_2$ and $C_3$, characterized by respective ratios by mass of the grafted copolymer (PVA/PEG) to the polydextrose of 1.2 and of 0.86, have respective degrees of gloss of 0.77 and 0.80, which are, respectively, 28.3% and 33.3% greater than that of tablet $E_{T3}$ coated using composition $T_3$ free of polydextrose.

4—Results Obtained with the Visual Method (i)—The gloss of the coated tables $E_{C1}$ and $E_{T1}$, expressed by the level of selection thereof by the members of a panel of 10 duly trained individuals, is evaluated according to the principle described in paragraph 2. The results obtained are reported in table 2 below:

TABLE 2

| | Coated tablet | |
|---|---|---|
| | $E_{C1}$ | $E_{T1}$ |
| % of selection of coated tablets considered to be the glossiest | 95.0% | 5.0% |

Tablet $E_{C1}$ coated using composition which is characterized by a ratio by mass of the grafted copolymer (PVA/PEG) to the polydextrose of 1.6, was considered to be the glossiest tablet by 95% of the members of the panel, whereas tablet $E_n$, coated using composition $T_1$ not comprising polydextrose, was selected by only 5% of the members of the panel as being the glossiest coated tablet.

(ii)—The gloss of the coated tablets $E_{C4}$, $E_{C5}$ and $E_{T4}$, expressed by the level of selection thereof by the members of the panel of 10 duly trained individuals, is evaluated according to the principle described in the preceding paragraph 2. The results obtained are reported in table 3 below:

TABLE 3

| | Coated tablet | | |
|---|---|---|---|
| | $E_{C4}$ | $E_{C5}$ | $E_{T4}$ |
| % of selection of coated tablets considered to be the glossiest | 43.75% | 31.25% | 25.0% |

Tablets $E_{C4}$ and $E_{C5}$ coated, respectively, using compositions $C_4$ and $C_5$, each characterized by an identical ratio by mass of the grafted copolymer (PVA/PEG) to the polydextrose of 0.6, were considered to be the glossiest tablets by 43.75% and 31.25%, respectively, of the members of the panel, or, cumulatively, to be the glossiest compounds by 75% of the members of the panel, whereas tablet $E_{T4}$ coated using composition $T_1$ comprising another polysaccharide, maltodextrin and a cellulose ether, was considered to be the glossiest by only 25% of the panel.

Method for Measuring Gloss Density Used for all the Measurements:

In order to demonstrate the gloss density of a sample, the latter is illuminated with a directive source at a given angle. A camera then makes it possible to obtain images. The areas which exhibit a high degree of gloss are thus localized.

This mapping method makes it possible to represent the spatial distribution of the gloss. It is then possible to extract therefrom the gloss density=number of pixels/mm$^2$.

Other Comparative Tests:

The table below highlights the results of four comparative trials.

Trial 1 uses a composition comprising Kollicoat (P1) and dextrin (P2) in a P1/P2 ratio 0.86 (therefore less than 3).

Trial 2 uses a composition comprising Kollicoat (P1) and Isomalt (P2) in an P1/P2 ratio=0.86 (therefore less than 3).

Trial 3 uses a composition in accordance with the present invention comprising Kollicoat (P1) and polydextrose (P2) in a P1/P2 ratio=0.86 (therefore less than 3).

Trial 4 uses a composition comprising Kollicoat (P1) and dextrin (P2) in a P1/P2 ratio=4 (therefore greater than 3).

|  | Gloss |
| --- | --- |
| Trial 1<br>Kollicoat IR = 30%<br>Dextrin = 35%<br>Kaolin = 18%<br>PEG 400 = 2%<br>Pigments = 15% | Gloss density: 267 |
| Trial 2<br>Kollicoat IR = 30%<br>Dextrin = 35%<br>Kaolin = 18%<br>PEG 400 = 2%<br>Pigments = 15% | Gloss density: 822 |
| Trial 3<br>Kollicoat IR = 30%<br>Polydextrose = 35%<br>Kaolin = 18%<br>PEG 400 = 2%<br>Pigments = 15% | Gloss density: 1521 |
| Trial 4<br>Kollicoat IR = 60%<br>Dextrin = 15%<br>HPMC = 10%<br>Glycerol = 5%<br>Pigments = 10% | Gloss density: 799 |

The gloss density was measured according to the method described above.

These results show in particular the surprising advantage provided by the selection of polydextrose as auxiliary agent, and also the importance of the value of the P1/P2 ratio, that must be less than 3.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A film-coated solid form intended for gastric use and having a glossy appearance, the film formed by a coating composition (C) comprising, per 100% of its mass:
   a) from 10% to 90% by mass of a grafted copolymer of polyvinyl alcohol and of polyethers ($P_1$); and
   b) from 90% to 10% by mass of an auxiliary coating agent, wherein a non-zero mass proportion of the auxiliary agent is polydextrose, and the ratio by mass of the grafted copolymer ($P_1$) to the polydextrose is less than or equal to 3, wherein the film-coating exhibits a gloss density of 1521 to 1707 and/or a degree of gloss of 0.77 to 0.80.

2. The film-coated solid form of claim 1, wherein the coating composition (C) also comprises from 2% to 30% by mass of a plasticizer or of a mixture of plasticizers.

3. The film-coated solid form of claim 2, wherein the coating composition (C) also comprises from 2% to 30% by mass of one or more coloring agents.

4. The film-coated solid form of claim 1, wherein the coating composition (C) also comprises from 2% to 30% by mass of one or more coloring agents.

5. The film-coated solid form of claim 4, wherein the coating composition (C) also comprises from 2% to 30% by mass of one or more inert fillers.

6. The film-coated solid form of claim 1, wherein the coating composition (C) also comprises from 2% to 30% by mass of one or more inert fillers.

7. The film-coated solid form of claim 6, wherein the coating composition (C) also comprises from 1% to 20% by mass of a glidant.

8. The film-coated solid form of claim 1, wherein the coating composition (C) also comprises from 1% to 20% by mass of a glidant.

9. The film-coated solid form of claim 8, wherein the ratio by mass of the grafted copolymer ($P_1$) to the polydextrose in the coating composition (C) is less than or equal to 3/2.

10. The film-coated solid form of claim 1, wherein the ratio by mass of the grafted copolymer ($P_1$) to the polydextrose in the coating composition (C) is less than or equal to 3/2.

11. The film-coated solid form of claim 1, wherein the ratio by mass of the grafted copolymer ($P_1$) to the polydextrose in the coating composition (C) is greater than or equal to 1/3.

12. The film-coated solid form of claim 11, wherein the ratio by mass of the grafted copolymer ($P_1$) to the polydextrose in the coating composition (C) is greater than or equal to 2/3.

13. The film-coated solid form of claim 1, wherein the ratio by mass of the grafted copolymer ($P_1$) to the polydextrose in the coating composition (C) is between 2/3 and 3/2.

14. The film-coated solid form of claim 1, wherein the coating composition (C) is in the form of an aqueous dispersion, a powder or ready-to-use granules.

* * * * *